(12) United States Patent
Andresen et al.

(10) Patent No.: US 6,335,790 B1
(45) Date of Patent: Jan. 1, 2002

(54) METHOD FOR DETERMINING THE SPATIAL CONCENTRATION OF THE COMPONENTS OF A GAS MIXTURE IN A COMBUSTION CHAMBER

(75) Inventors: Peter Andresen, Dransfeld; Gerhard Lepperhoff, Stolberg, both of (DE)

(73) Assignee: Lavision GmbH, Gottingen (DE)

( * ) Notice: Subject to any disclaimer, the term of this patent is extended or adjusted under 35 U.S.C. 154(b) by 0 days.

(21) Appl. No.: 09/588,140

(22) Filed: Jun. 2, 2000

(30) Foreign Application Priority Data

Jun. 4, 1999 (DE) .......................... 199 25 583

(51) Int. Cl.[7] .............................. G01B 9/021
(52) U.S. Cl. ....................... 356/347; 356/342
(58) Field of Search ................ 356/432, 433, 356/434, 437, 438, 440, 336, 337, 338, 342; 250/339.13, 340, 573, 222.1, 574; 73/24.02, 24.06

(56) References Cited

U.S. PATENT DOCUMENTS 3,317,730 A * 5/1967 Hilsum
5,244,809 A * 9/1993 Nowak .......................... 436/56
5,425,916 A * 6/1995 Beer et al. ..................... 422/62
5,641,972 A * 6/1997 Breda .......................... 356/338
5,751,416 A * 5/1998 Singh et al. ................. 356/311

FOREIGN PATENT DOCUMENTS

DE          4320943 A1    1/1995

* cited by examiner

Primary Examiner—Hoa Q. Pham
(74) Attorney, Agent, or Firm—Thomas R. Vigil

(57) ABSTRACT

The invention relates to a method for determining the spatial concentration of the various components of a mixture, in particular of a gas mixture in a combustion chamber, of a motor for example; a laser beam is hereby directed into the combustion chamber; the laser beam brings the particles of the mixture to radiate, whereas this light of the particles is passed backward through a masked lens and is imaged on a display as a radiating surface and the radial intensity distribution is recorded by an array photodetector, whereas the spatial concentration of individual components of the particle mixture may be measured from the radial intensity distribution.

7 Claims, 2 Drawing Sheets

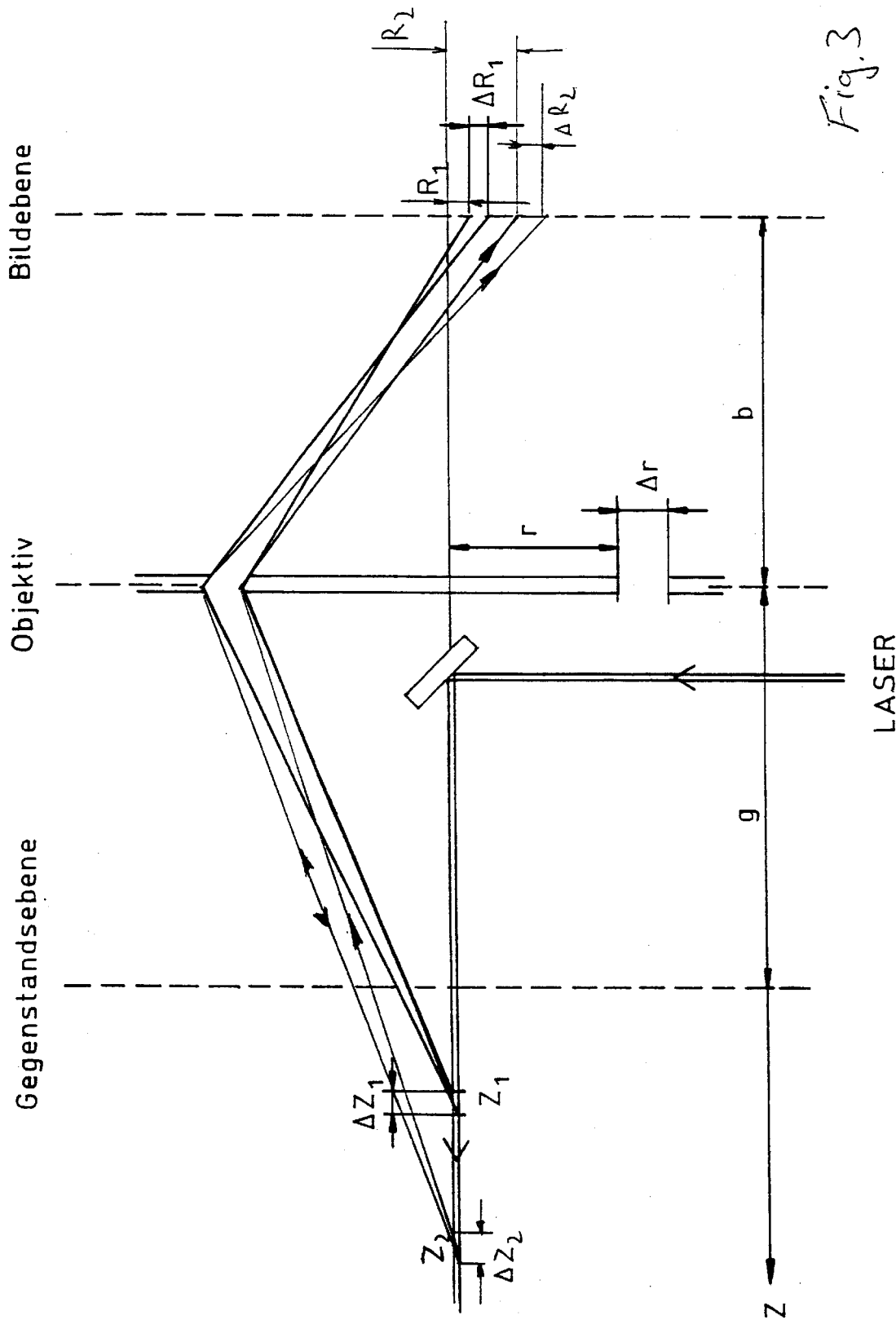

METHOD FOR DETERMINING THE SPATIAL CONCENTRATION OF THE COMPONENTS OF A GAS MIXTURE IN A COMBUSTION CHAMBER

BACKGROUND OF THE INVENTION

1. Field of the Invention

The invention relates to a method for determining the spatial concentration of the various components of a mixture, in particular of a gas mixture in a combustion chamber, of a motor for example.

2. Description of the Prior Art

A method of the type mentioned above is known from internal combustion engines for example; several ports are hereby provided in the combustion chamber, in a cylinder e.g., whereas the spatial concentration of the different components in the fuel-air mixture including potential residual gases is detected by means of optical devices, e.g. by means of mirrors. Knowledge of the local concentration of the different components of such a mixture, for example of a mixture of fuel, oxygen, nitrogen and residual gas is needed for the optimization of combustion in the combustion chamber. Since the state of the art requires a plurality of ports—at least two ports for the spatial determination of the concentration of the gas mixture are needed—construction implies quite complicated measures to make such a determination possible. So-called "glass motors" are also known, which also offer the possibility to optically record the concentration of different gases in a gas mixture in the combustion chamber.

All these known methods and devices have as a common drawback not only the fact that their construction is complicated but also, and this is much more important, that the real flow and combustion conditions are falsified since the creation of the optical port often involves great changes in the geometry of the combustion chamber. Changes in the combustion chamber geometry always affect however the processes of combustion, too. Therefore, the combustion chamber should be altered as little as possible by the optical port on one side. On the other side however, measurements should be made possible and should be as detailed as possible, as e.g. local detailed measurements of gas concentrations.

By using only one aperture, optical measurements could also be made on hardly changed series production engines by removing for example the pressure absorber or the spark plug and by replacing it by an optical port.

SUMMARY OF THE INVENTION

The object of the present invention is therefore to provide a method and a device with the help of which the expenditure needed to determine the spatial concentration of the various components of a gas mixture in a space, in particular in a combustion chamber, may be minimized, but that still yields accurate results.

According to the present invention, a laser beam is hereby directed through one unique aperture arranged in the combustion chamber, whereas the laser beam brings particles of the mixture situated on one line to radiate, whereas the light emitted by the particles is then passed backward through the same aperture and is focused on a light-sensitive surface (e.g. on an intensified CCD-camera) to form an image via a specially darkened lens. The particles are so strongly excited by the laser beam that they emit photons. The photons bring the light-sensitive surface to radiate. The brightness of the particles and the size of the radiant surface on the light-sensitive surface permits to determine locally and separately the concentration of the particles along the line defined by the laser by means of an array photodetector (e.g. an intensified CCD-camera).

The important point is that the emissions induced on one line are recorded backward as photons so that only one optical port is needed, whereas the local course of concentration may still be determined.

It is well known that by choosing or acquiring certain optical parameters (such as the wave length and the polarization of the exciting laser, the wave lengths of the light radiated by the particles, the analysis of the polarization or the duration of radiation) it is possible to identify the individual components of a particle mixture and to also determine separately the concentration of individual components by adequate measures (e.g. filtration). Radiating substances (tracers, e.g. colours) may be added to the components of the gas mixture (e.g. air, fuel or combustion gas) in order to deduce the concentration of the corresponding components from the radiation of these additives.

The method foots on the cognition that a laser emits light with a specific wave length that brings the particles of the gas mixture to radiate. The wave length of the light emitted by the particles upon excitation through the laser depends on the type of the particles, whether the particles involved are oxygen molecules, fuel molecules, nitrogen molecules or tracer molecules added to substances.

In order to determine the concentration of individual particles or molecules in the combustion chamber at different places, the reasoning made with reference to a projection lens is that particles or objects in general illuminate on the focal plane a surface that gets bigger in size as they are located farther away from the plane of object. Defining z as the distance between the focal plane and the plane of object ($z=0$ for the plane of object), the points radiating in the focal plane provide circular surfaces that get bigger in size the farther they are from the plane of object. Radiating points located at different distances z from the plane of object on the line defined by the laser hence provide circular surfaces of different size in the focal plane.

To limit backward the light beam emitted by the particles is particularly important. By masking centrally the beam of rays emerging from one source, the surface projected in the focal plane is no longer circular but is a circular ring having a radius R and a thickness $\Delta R$. The thickness of the circular ring is getting smaller when the beam is increasingly limited in diameter. In this arrangement, the radiation occasioned by the laser in a spatial area $[z_1, z_2]$ is imaged on the focal plane in a radial area $[R_1, R_2]$. The number of photons emitted in the spatial area $[z_1, z_2]$ may be determined from the integration of the radiation intensity recorded in the radial area $[R_1, R_2]$. The number of emitted photons permits to determine the concentration of the particles according to well known procedures, e.g. Raman scattering.

By luminating one line in the combustion chamber by means of a laser, a system of concentric circular rings is created in the focal plane, whereas the light recorded at different radial intervals may be allocated to different sources on the laser line. The local concentration of individual components of a gas mixture in a combustion chamber is thus possible, since the distance separating the concentration of particles from the plane of object, and hence from the cylinder wall, can be determined.

A semireflecting mirror may possibly be arranged in the beam path of the laser. By having a mirror arranged in the beam path of the laser, it is possible to introduce the laser beam through the same port in the cylinder through which the light emitted by the particles is coming out. The important fact is that, thanks to this method according to the invention, only one port into the combustion chamber is needed to send the laser through this port into the combustion chamber and to receive the light emitted by the particles.

The array to carry out the previously described method is characterized by a laser, a mirror arranged in the beam path of the laser as well as by a lens arranged in the beam path of the light emitted by the particles, a display being arranged behind said lens. The lens is hereby opaquely covered on its centre in order to achieve an increased selectivity.

The invention will be explained more explicitly in the following with the help of the drawing illustrating an example thereof.

BRIEF DESCRIPTION OF THE DRAWING

FIG. 3 is a schematic illustration of the beam path of two luminous regions located behind the plane of object and imaged on the focal plane.

DESCRIPTION OF THE PREFERRED EMBODIMENT(S)

Figure 1:
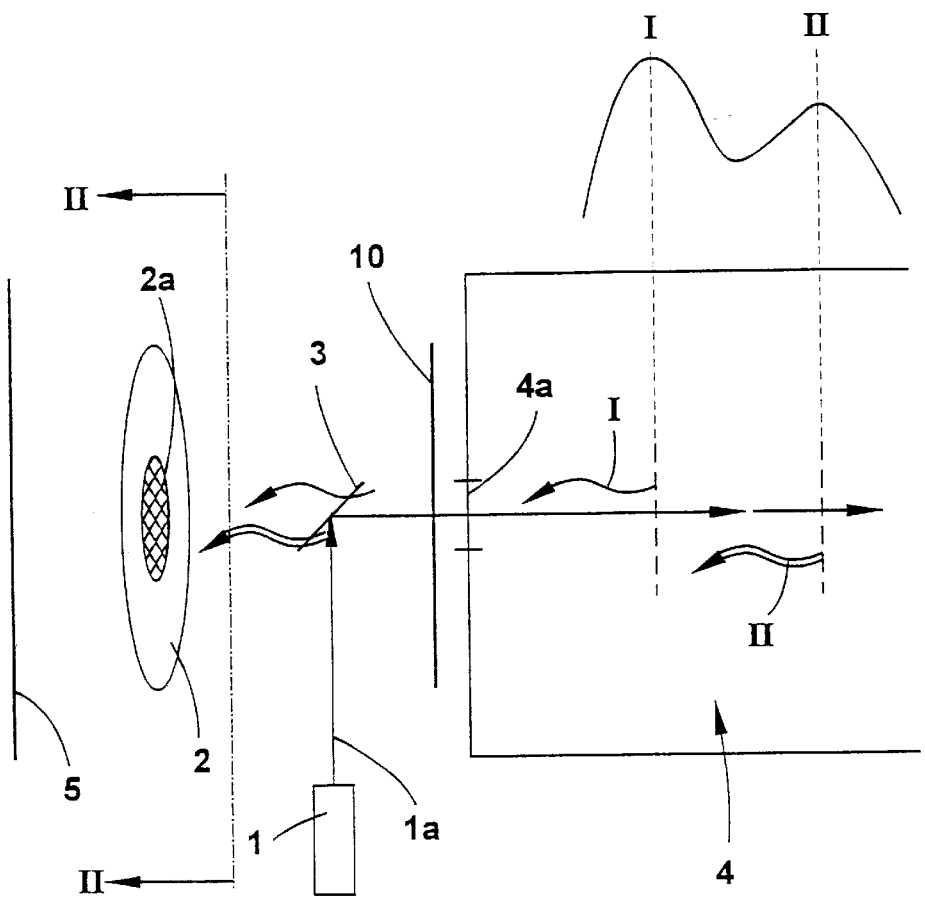
FIG. 1 is a schematic illustration of the arrangement for determining the spatial concentration of individual particles of a mixture.

According to FIG. 1, the laser is referred to with numeral 1. The laser emits a laser beam 1$a$ that is directed by the semireflecting mirror 3 through a window 4$a$ into the combustion chamber 4. The combustion chamber 4 contains a gas mixture, in which the component to be detected is represented together with the course of concentration by means of the curve (illustrated above the schematic illustration of the combustion chamber) and is brought to radiate on the line defined by the laser. The two concentrations I and II of a gas are present at two specific locations. The component to be detected may for example be oxygen, nitrogen or fuel or tracer molecules contained in the gas mixture. In the area of the concentration I and II, the laser beam 1$a$ strikes the corresponding particles and brings them to radiate, whereas the intensity of the radiation is proportional to the concentration. The light induced by the laser is sent back through the window 4$a$, traverses the semireflecting mirror and is focused by the lens 2 on the focal plane referred to with numeral 5 where it appears as a ring-shaped radiating surface. In its centre, the lens 2 may for example be covered by an opaque foil 2$a$. The lens 2 focusses the light from the plane of object 10 onto the focal plane 5, in which the intensity of the backscattered light is recorded two-dimensionally by a photodetector.

Only the plane of object 10 is sharply defined on the display by the lens. If the beam spot, that is the radiating particle, is not located on the plane of object 10, but at a distance z behind 10, the beam spot on the focal plane is out of focus and is a disk with a more or less homogeneous distribution of intensity.

Figure 2:
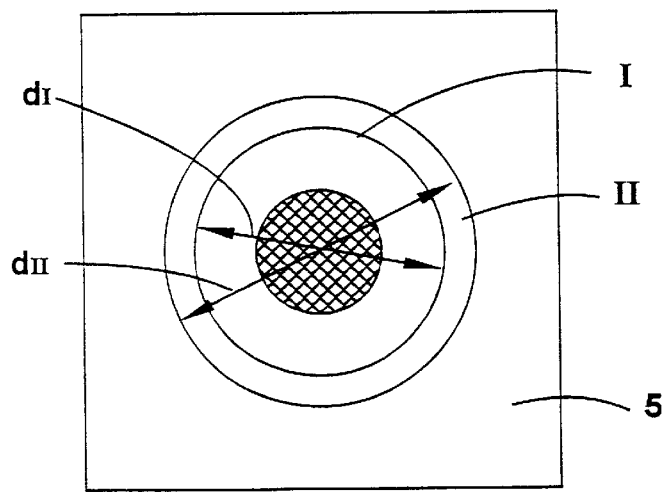
FIG. 2 is a view taken along the line II/II of FIG. 1.

But if the center of the lens is covered (advantageously symmetrically in the Fourier plane), only the light of the beam spot that passes through the remaining annular gap in lens 2 reaches the display on the focal plane. In this case, the image formed by the lens covered in its center does not represent a disk, but a circular ring. The narrower the annular gap, the smaller the width of the circular ring. Since the radius or the diameter of the circular ring increases uniformly as the beam spot moves away from the focal plane, the distance $z_0$ of the particle to the plane of object may be deduced from the radius of the circular ring. Accordingly, two concentric, circular rings I and II are originating, as may be seen in FIG. 2. By integrating the recorded light intensity by way of the surface of the two rings, conclusions may now be drawn regarding the degree of concentration of the corresponding particles, e.g. oxygen and nitrogen, at the locations I and II, whereas the size of the diameter permits to draw conclusions regarding the spatial distance separating the concentration I and II from the plane of object 10.

In the illustration according to FIG. 3, the laser is bunched by a mirror on the optical axis R1 of the image and only brings particles to radiate that are located on the line defined by the laser. The lens is masked in such a way that light is only allowed to pass in the region $\Delta r$. Hence, the radiation of the particles in the region $\Delta Z$ is only imaged in the region $\Delta R$ on the focal plane.

FIG. 3 shows two radiant regions $\Delta Z1$ and $\Delta Z2$ in particular, said regions being imaged on the focal plane with $\Delta R1$ and $\Delta R2$.

It is hereby ascertained that the smaller the distance [$Z_1$, $Z_2$] separating the radiant region from the plane of object, the farther the image region $\Delta R_1$, $\Delta R_2$ from the optical axis [$R_1$, $R_2$]. With regard to the size of the image region on the focal plane relative to the radiant region, the following relation is true: $\Delta r/y \approx \Delta Z/Z$, whereas Z is the distance separating the radiant region from the plane of object.

We claim:

1. A method for determining the spatial concentration of the various components of a gas mixture in a combustion chamber,
   characterized by the steps of:
      providing an enclosed combustion chamber;
      providing only one observation aperture in a wall of the chamber;
      directing a laser beam through the only one aperture into the combustion chamber, where the laser beam rings specific particles of the mixture situated on one line to radiate back-scattered light;
      imaging the back-scattered light of these particles as a radiating surface by a masked lens;
      recording locally in detail the intensity distribution; and,
      measuring the concentration of the individual components situated along the laser line locally in detail from the radial distribution of intensity.

2. A method according to claim 1,
   characterized in that a semi-reflecting mirror is arranged in a path of the laser beam.

3. A method according to claim 1,
   characterized in that, in order to image highly precise rings on a display, the lens is opaquely covered in its central part.

4. A method according to claim 1,
   characterized in that the radiating surface is imaged on a display.

5. A method according to claim 4,
   characterized in that the distribution of intensity is recorded locally and in detail on the display by an array photodetector.

6. An arrangement for performing the method according to claim 1 characterized by a laser that is bunched into the combustion chamber through only one aperture, a semi-reflecting mirror being arranged in the beam path of the laser, a lens being arranged behind the display in the beam path of the back-scattered light by a locally resolving photodetector.

7. An arrangement according to claim 6, characterized in that the lens is opaquely covered in its central part.

* * * * *